United States Patent
Bouton

(10) Patent No.: US 9,011,334 B2
(45) Date of Patent: Apr. 21, 2015

(54) ACCESS DISCONNECT DETECTION

(75) Inventor: Chad E. Bouton, Powell, OH (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1726 days.

(21) Appl. No.: 11/862,697

(22) Filed: Sep. 27, 2007

(65) Prior Publication Data

US 2009/0088612 A1    Apr. 2, 2009

(51) Int. Cl.
| A61B 5/00 | (2006.01) |
| A61B 5/02 | (2006.01) |
| A61M 37/00 | (2006.01) |
| A61M 1/36 | (2006.01) |

(52) U.S. Cl.
CPC .......... *A61M 1/3653* (2013.01); *A61B 5/02042* (2013.01); *A61M 1/3656* (2014.02)

(58) Field of Classification Search
CPC ........... A61B 5/02042; A61M 1/3653; A61M 1/3656
USPC ................. 600/500, 504; 604/65, 66, 67, 604/4.01–6.16
See application file for complete search history.

(56) References Cited

U.S. PATENT DOCUMENTS

| 4,499,214 | A | | 2/1985 | Sortwell |
| 4,501,828 | A | | 2/1985 | Hadermann et al. |
| 5,241,964 | A | * | 9/1993 | McQuilkin ................. 600/485 |
| 5,332,524 | A | | 7/1994 | Kaylor |
| 5,427,645 | A | | 6/1995 | Lovin |
| 6,071,421 | A | | 6/2000 | Brown |
| 6,077,443 | A | * | 6/2000 | Goldau ......................... 210/741 |
| 6,090,048 | A | * | 7/2000 | Hertz et al. .................. 600/485 |
| 6,098,466 | A | * | 8/2000 | Shkarlet ..................... 73/861.25 |
| 6,167,765 | B1 | * | 1/2001 | Weitzel ...................... 73/861.18 |
| 6,221,040 | B1 | * | 4/2001 | Kleinekofort ................... 604/65 |
| 6,246,482 | B1 | | 6/2001 | Kinrot et al. |
| 6,567,700 | B1 | * | 5/2003 | Turcott et al. ..................... 607/9 |
| 7,801,583 | B2 | * | 9/2010 | Brabrand ..................... 600/382 |
| 2001/0007930 | A1 | * | 7/2001 | Kleinekofort ................ 604/4.01 |

(Continued)

FOREIGN PATENT DOCUMENTS

| DE | 19734002 C1 | 9/1998 |
| WO | 02/053025 A2 | 11/2002 |

(Continued)

OTHER PUBLICATIONS

U.S. Appl. No. 11/673,390, filed Feb. 9, 2007.

(Continued)

*Primary Examiner* — Michael D'Angelo
*Assistant Examiner* — Christian Jang
(74) *Attorney, Agent, or Firm* — K&L Gates LLP

(57) ABSTRACT

Techniques are disclosed for monitoring the flow of blood returning to a patient from an extracorporeal therapy machine, such as a hemodialysis machine or an apheresis machine. Blood returning from such a machine is pumped, typically by a peristaltic pump, which returns the blood in pulsed flow or pulses. This flow can be sensed by Doppler flow sensors or accelerometers as it returns to the patient. If the flow is interrupted by dislodgement of the venous access needle, or by leaking of blood from the needle, these sensors will detect significantly different flow or vibrations. A controller can then cease therapy, alert a caregiver, or sound an alarm.

15 Claims, 7 Drawing Sheets

(56) References Cited

U.S. PATENT DOCUMENTS

| | | |
|---|---|---|
| 2002/0198483 A1 | 12/2002 | Wariar et al. |
| 2004/0039420 A1* | 2/2004 | Jayne et al. ............... 607/5 |
| 2004/0171977 A1* | 9/2004 | Paolini et al. ............ 604/4.01 |
| 2005/0095171 A1* | 5/2005 | Fressinet et al. ............ 422/44 |
| 2005/0131288 A1* | 6/2005 | Turner et al. ............. 600/391 |
| 2006/0130591 A1 | 6/2006 | Perkins |
| 2006/0178616 A1* | 8/2006 | Hartman et al. ............ 604/65 |
| 2008/0065006 A1 | 3/2008 | Roger |
| 2008/0167563 A1* | 7/2008 | Trandafir ................. 600/504 |
| 2008/0183287 A1* | 7/2008 | Ayre ..................... 623/3.28 |
| 2008/0195021 A1* | 8/2008 | Roger et al. ............. 604/4.01 |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088613 A1 | 4/2009 | Marttila |
| 2009/0088683 A1 | 4/2009 | Roger et al. |
| 2009/0105627 A1 | 4/2009 | Rohde |
| 2010/0022934 A1 | 1/2010 | Hogard |
| 2010/0022935 A1 | 1/2010 | Muller |

FOREIGN PATENT DOCUMENTS

| | | | |
|---|---|---|---|
| WO | WO 2005/046439 | * | 5/2005 |
| WO | 2006/044677 A1 | | 4/2006 |
| WO | PCT/US2008/066114 | | 10/2008 |

OTHER PUBLICATIONS

U.S. Appl. No. 11/859,589, filed Sep. 21, 2007.
U.S. Appl. No. 11/859,561, filed Sep. 21, 2007.
U.S. Appl. No. 11/865,531, filed Oct. 1, 2007.
U.S. Appl. No. 12/180,331, filed Jul. 25, 2008.
European Office Action issued Jan. 7, 2014 for related European Appln. No. 08770331.0.

* cited by examiner

ACCESS DISCONNECT DETECTION

BACKGROUND

The invention is in the field of medical treatments generally and patient vascular access systems. The present invention relates to embodiments for detecting blood leakage during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from complications that can arise from continuing therapeutic procedures, and even from diagnostic procedures, that are necessary for their continued care. Treatments involving extra-corporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle. Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery or an arteriovenous fistula/graft, and a needle and a pump are used to provide the blood to the therapeutic machine. It is relatively simple to detect a problem with withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. For example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

One embodiment is an accelerometer-based access disconnect detector. The detector includes an accelerometer configured for mounting on a patient near an access site, signal processing circuitry, the signal processing circuitry operably connected to the accelerometer for receiving indications from the accelerometer, and a controller configured for receiving readings from the signal processing circuitry and for sending a signal upon a change in the readings, wherein the controller is in communication with or is part of a therapy machine for receiving blood and returning blood to a patient.

Another embodiment is an access disconnect detector. The detector includes a sensor for determining a flow of blood in a vein of a patient, the blood being returned from an extracorporeal blood therapy and the sensor configured for mounting on the patient near an access site, signal processing circuitry, the circuitry operably connected to the sensor for determining a flow rate of blood being returned from the extracorporeal therapy, and a communications circuit connected to the signal processing circuitry, wherein the sensor is configured for sensing the flow rate of blood through the vein and for generating readings indicative of the flow, and the signal processing circuitry is configured for receiving the readings and sending the readings to the communications circuit.

Another embodiment is a method for detecting an access disconnection. The method includes steps of mounting a sensor on a patient near an access site, establishing a baseline sensor reading of the patient, detecting readings indicative of a pulsatile flow of blood with the sensor, comparing additional readings during an extracorporeal blood therapy with the readings indicative of pulsatile flow, deciding whether the additional readings are significantly different from the readings of pulsatile flow, and sending a signal if the sensor readings are significantly different from the readings of pulsatile flow.

Another embodiment is a sensor-based method for detecting blood flow. The method includes steps of mounting a sensor indicative of blood flow to a patient near an access site, detecting first readings from the sensor indicative of a flow of blood from a pulsing mechanical pump, beginning an extracorporeal therapy with the patient, monitoring additional readings from the sensor during the therapy, deciding whether the additional readings are different from the first readings, and sending an alert if the readings are different from the first readings.

Additional features and advantages are described herein, and will be apparent from, the following Detailed Description and the figures.

DETAILED DESCRIPTION

Figure 1:
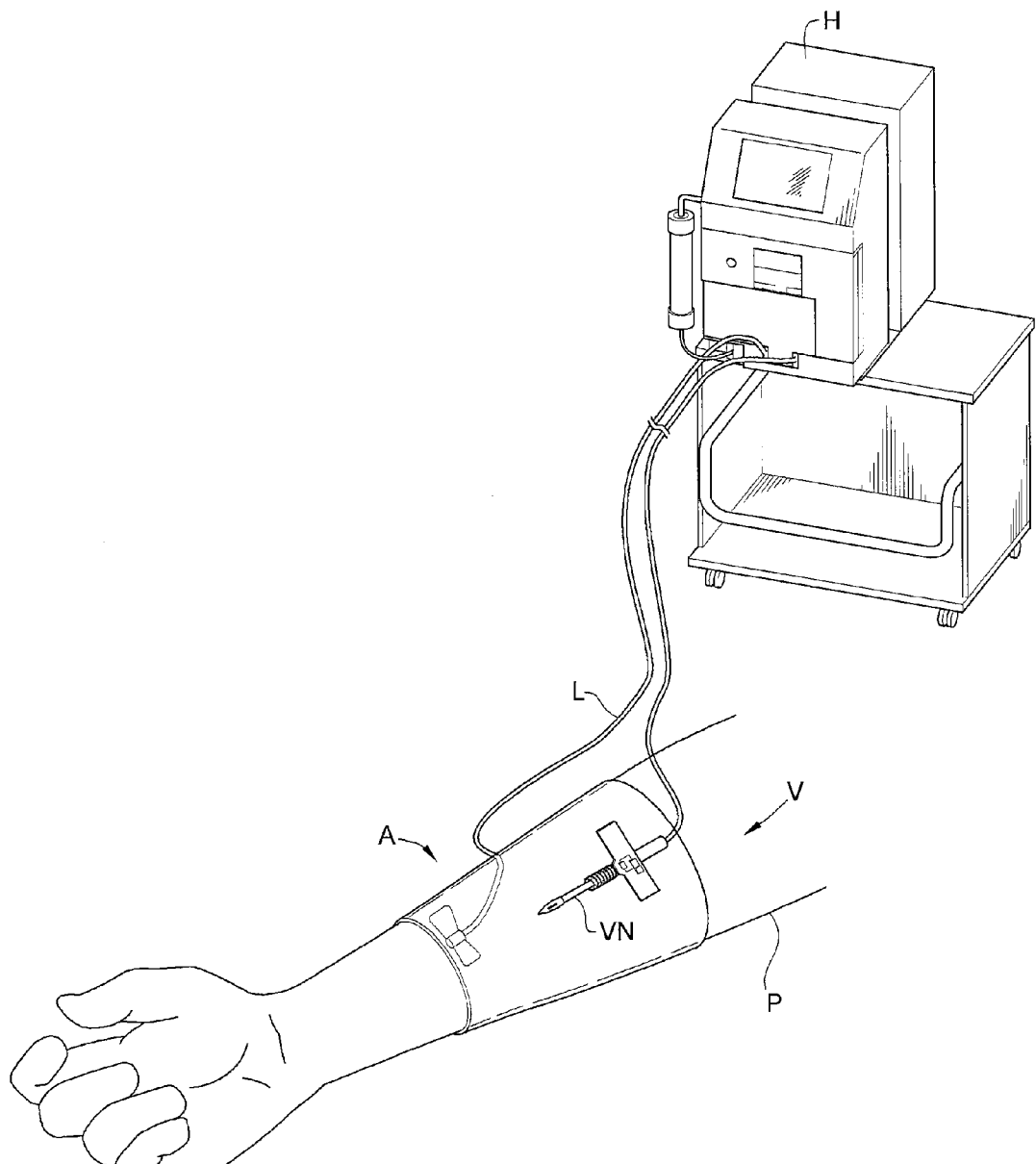
FIG. 1 is a prior art view of an access site on a patient.

As noted, it is important to detect a needle disconnect from an access site as soon as possible after it has happened. Embodiments of the present invention are useful for monitoring an access site in which a patient receives extracorporeal blood therapy, such as a person undergoing hemodialysis with a hemodialysis machine. An example of such a situation is depicted in FIG. 1, which depicts a patient P undergoing hemodialysis with a hemodialysis machine H. The patient is connected to the hemodialysis machine with tubing lines L connected to an arterial access site A and a venous access site V. Venous access site needle $V_n$ is depicted. Other extracorporeal treatments are also contemplated, such as apheresis.

Figure 2:
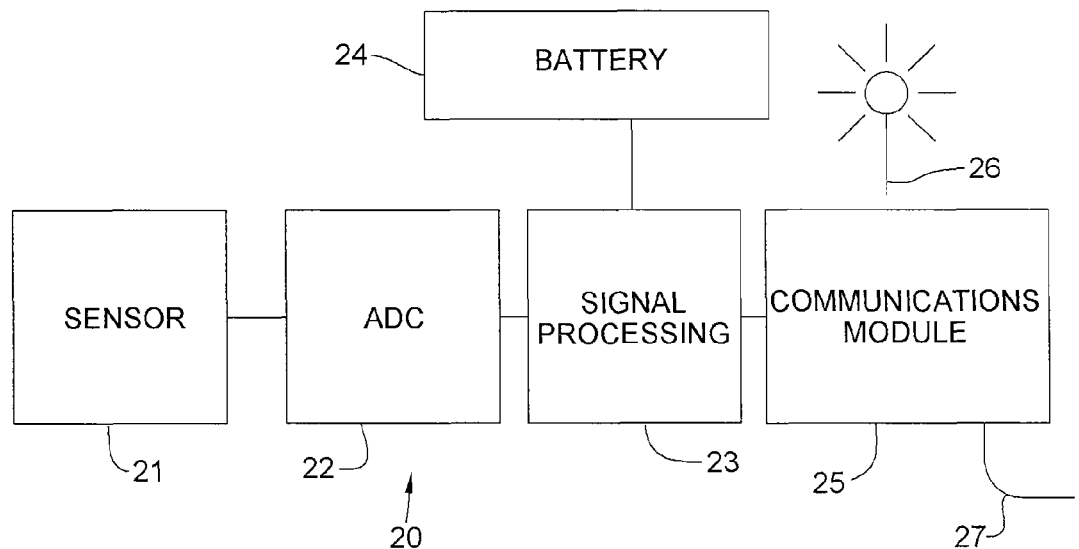
FIG. 2 is a schematic view of a first embodiment of an access disconnect system.
Figure 3:
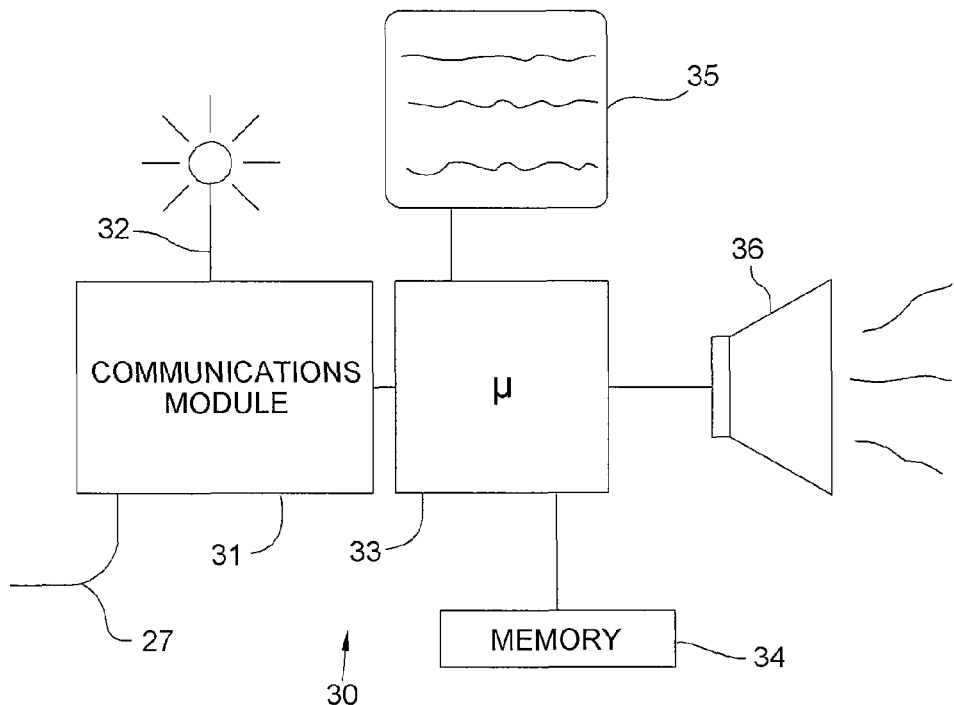
FIG. 3 is a schematic view of a control system for access disconnect detection.

A first embodiment of an access disconnect detection system is disclosed in FIGS. 2-3. The embodiment in FIG. 2 is a sensor and its associated circuitry for placement on the patient near or adjacent the access site, that is, near or adjacent the venous needle insertion point, usually on an arteriovenous fistula site. The sensor 21 includes or is operably connected to an analog-to-digital converter (ADC) 22 and to further signal processing 23, which may convert the digital data to a preferred format for transmission via communications module 25. The communications module 25 is a wireless module with an antenna 26, as shown. In other embodiments, the communications module is connected for further processing via a cord or wire 27.

The data is received at a communications module 31 of a receiver circuit 30. This circuit may be in communication with, or may itself be part of, a therapy machine, such as a hemodialysis machine. Communications module 31 may be a wireless transmitter/receiver with an antenna 32. The receiver circuit includes a microcontroller 33 and a memory 34. Memory 34 may include a computer program and a look-up table for values of sensor readings and the proper steps to take according to the reading. The microcontroller and memory include circuitry and logic sufficient to receive signals from the sensor and the signal processing module and to receive, process and interpret those signals. The microprocessor also includes sufficient logic, in the form of software on a computer readable medium, to interpret the sensor data and to use the look up table to determine whether the readings suggest that the flow of blood has slowed, slowed to a great extent, or has stopped.

One possible step to take, if the sensor reading so indicates, is to send a signal, such as an alarm using a local output device, such as a video screen 35 or a speaker 36. This will alert the patient or a caregiver that a blood leak has been detected or that the needle may have become disconnected from the access site. The receiver may also send a signal through the communications module to a remote computer, such as a hospital or clinic information system, or to so send an alert to other personnel or to other sites.

Accelerometer Application

The sensor contemplated in one embodiment is an accelerometer. An accelerometer is a device for measuring external force. In this instance, the force is the pulsatile force of the patient's blood returning to the patient through the fistula. The accelerometer will sense the vibrations of the pulsed flow, at about the rate of the pump which is pumping the blood. This is typically a peristaltic pump, which rotates at a certain rate of revolutions per minute. Other mechanical pumps may be used, such as shuttle pumps or linear drive pumps. Even though the certain rate of revolutions per minute of the pump is close to a rate of a normal heartbeat of from about 50 to about 85 beats per minute, it is easily distinguished, because the accelerometer is mounted within 1-2 cm of the access site, and thus the vein into which the blood is being returned. Accordingly, the signal from the flow into the vein from the therapy machine is expected to be significantly stronger than the beat of the heart of the patient, which is more remote from the access site.

A number of accelerometers are available from many manufacturers, such as Measurement Specialties, Inc., Hampton, Va., and Endevco Corp., San Juan Capistrano, Calif. One example is Model 40366 from Endevco. This is a microelectronic mechanical systems, capacitance-type accelerometer, including a very small mass and size, less than a cube 3 mm on a side. Such accelerometers are very small and lightweight, and may be assembled and mounted with some or all of the circuitry discussed above. In one embodiment, the accelerometer and at least some of the circuitry is mounted on the patient using medically-acceptable adhesive, such as a cyanoacrylate. In other embodiments, the accelerometer is part of a housing or detector that is taped to the patient's arm or other area, so that the accelerometer is suitably near the access site and can detect the vibrations of the pulsating flow of the returning blood.

The signal processing circuitry and wireless transmitter are small and compact, and are easily placed on the patient at the access site. One signal module that fits the needs for this application is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). One or more sensors are connected to the module. The module in FIG. 2 includes an analog-to-digital (ADC) converter to convert analog data from the sensor into digital data. The digital data is thus formatted when it is routed to a data buffer before wireless transmission or conveying via cable to a remote site. The remote site can be a nearby table within a few feet of the patient, or the hemodialysis machine, or a communications portion of the hemodialysis machine in the same room with the patient.

Figure 4:
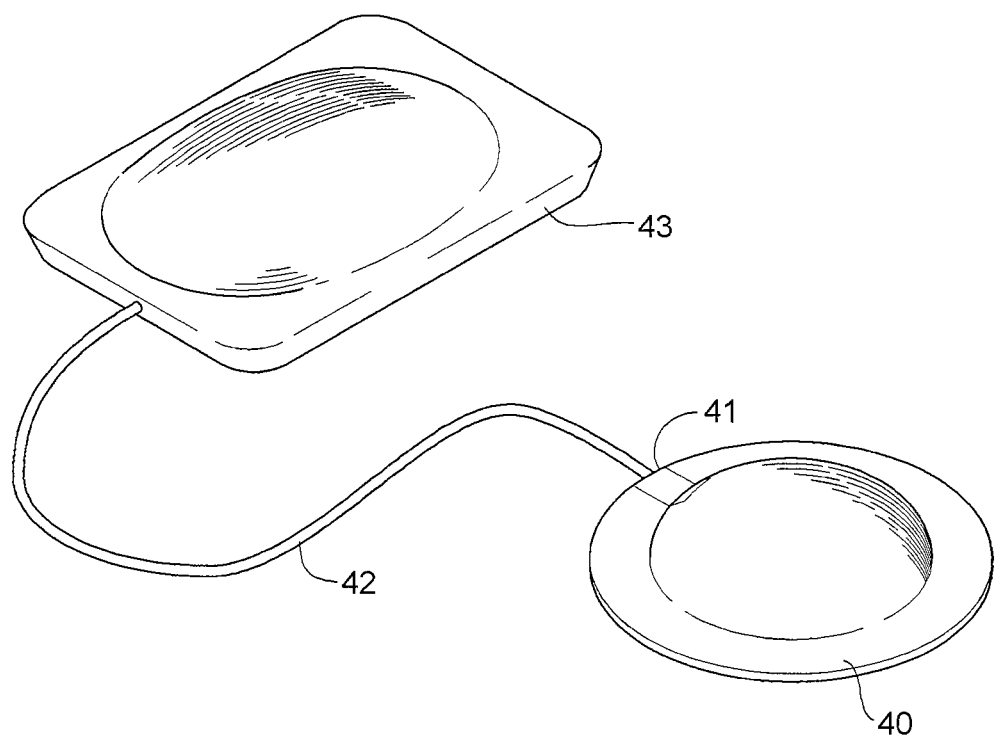
FIGS. 4-6 depict embodiments with an accelerometer sensor.
Figure 5:
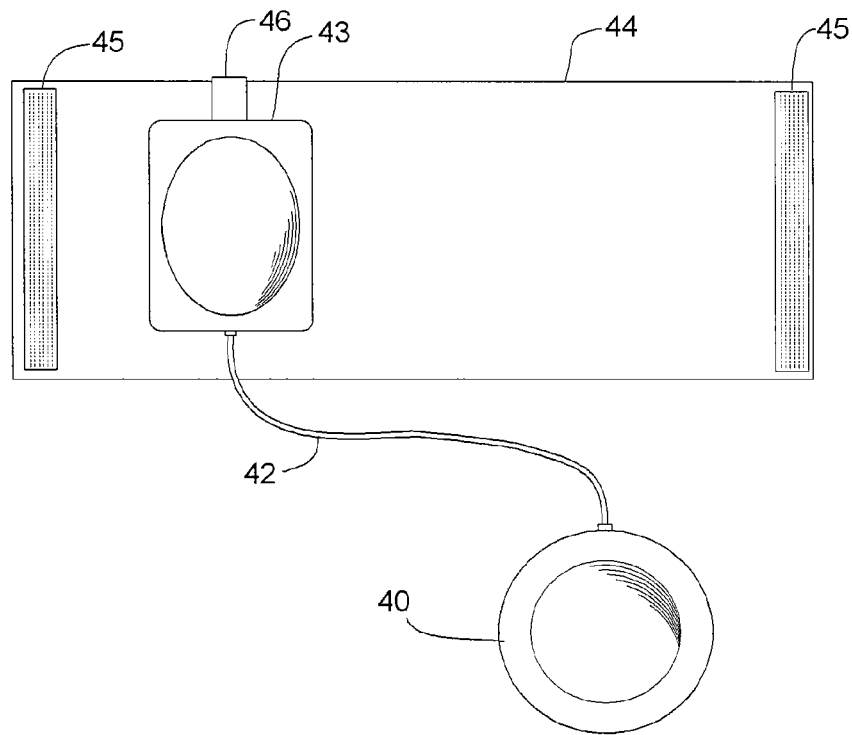
Figure 6:
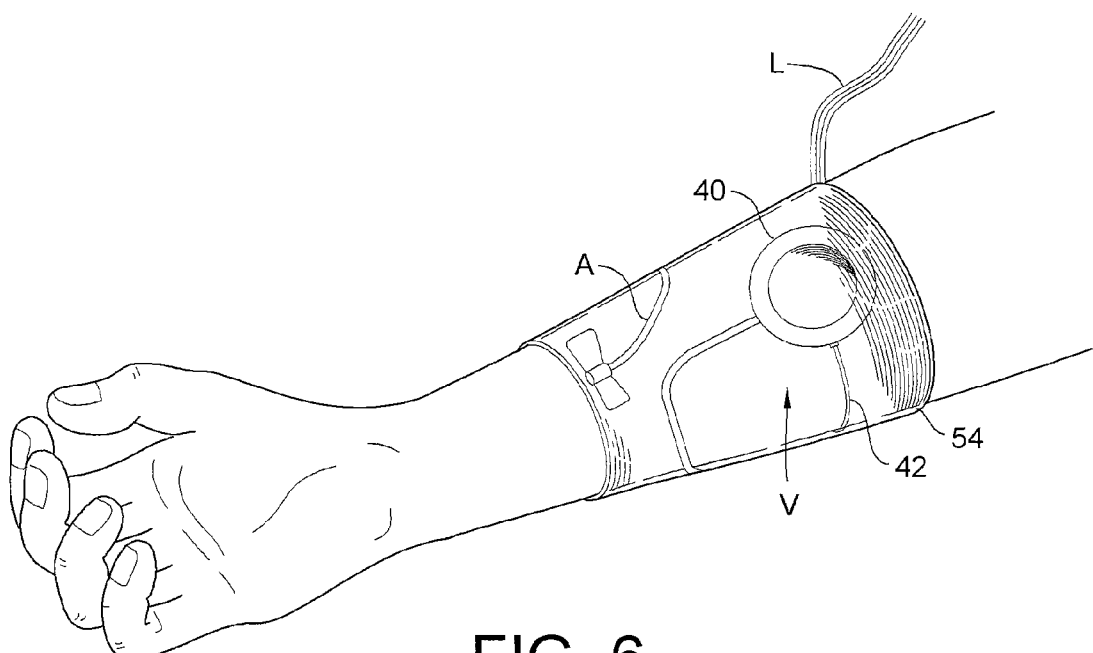

Embodiments of the accelerometer sensor and a blood flow detector using the sensor are depicted in FIGS. 4-6. In FIG. 4, an accelerometer 41 is placed into a housing 40 for easier and steady placement on a patient. The accelerometer is placed near an edge of the housing so that the accelerometer may be as close as possible to the return vein of the access site. The housing may be a flexible silicone pad, or other conformable material that is not irritating to the patient. The sensor is connected by cord 42 to a receiver module 43. Cord 42 may only be one or two feet long (30-60 cm) so that the receiver module 43 may be placed in a shirt or pajama pocket of the patient.

Receiver module 43 may include a battery to power the accelerometer signal conversion circuits, and may also include a microcontroller and sufficient logic and memory to convert and analyze the signals sent from the accelerometer. Receiver module 43 may itself have a communications module with a wireless capability. The receiver module and microcontroller have the capability to communicate with the hemodialysis machine or other therapy machine, or with another receiver circuit or controller in operable communication with the therapy machine. Upon detecting cessation of the flow of blood, or a significant lessening of the flow, the microcontroller may send a signal. The signal may order the therapy to be ceased, may order an alarm to be sounded on a local output, or may send an alert to the patient or to a caregiver.

Another embodiment is presented in FIGS. 5-6. In these figures, the sensor and the housing 40 are used in conjunction with an arm band 44 having hook-and-loop fastener strips 45. These strips are available under the trade name Velcro®. The receiver module 43 is mounted on outside of the arm band 44 and may use a clip 46. On the patient's arm near the access site, housing 40 is secured over the venous access site V with an additional securing bandage 54. In other embodiments, the housing may be firmly secured to the access site with tape.

Figure 7:
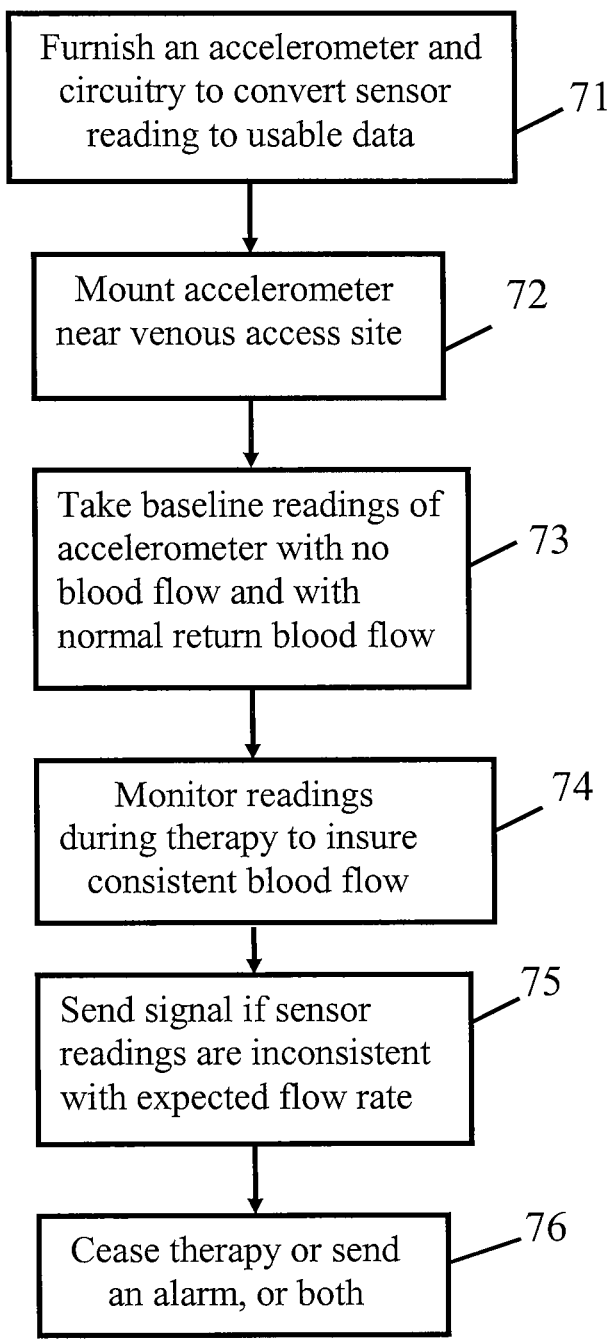
FIG. 7 is a flowchart depicting a method of using an accelerometer at an access site.

A method of using the accelerometer is depicted in the flowchart of FIG. 7. In a first step of the method, an accelerometer is furnished 71, along with circuitry to convert the sensor data, typically analog signals, into usable digital data. Other embodiments may simply use analog data, since no conversion to digital is strictly required, although it is customary. The accelerometer is mounted 72 near the venous access site, so that the readings of blood movement are clearly discernable. Baseline readings are taken 73, typically with both no flow and with normal return blood flow in order to calibrate the accelerometer and to orient the microcontroller or other logic circuit with what are normal and non-normal blood flows.

After therapy has begun, the accelerometer is monitored 74 to determine whether the sensor readings are consistent with normal blood flow. If the sensor readings are inconsistent with the expected flow, the microcontroller or other logic-device sends 75 a signal. As noted above, the signal may be a signal to cease therapy 76, or may be a signal to raise alert or to send an alarm through a local output device, such as a video screen or a speaker. There are other embodiments using an accelerometer to detect blood flow, and this description is not intended to limit the embodiments.

Flow Sensor Application

Another sensor option is to use an ultrasound probe, such as a Doppler flow sensor, to detect blood flow in the vein receiving the blood. The Doppler probe is mounted on the patient's arm, near or preferably atop the vein receiving the blood. The Doppler will detect the blood flow, and if access disconnect occurs, the sensing signals will cease or change. Software or logic in a controller for the sensor or in the therapy machine will note the change. If the change is sufficient to suggest that corrective action should be taken, the microcontroller or other circuitry sends a signal to alert a caregiver or to cease pumping blood from the patient.

Doppler sensors are made by many manufacturers, including Parks Medical Electronics, Las Vegas, Nev., including pencil probes. Probes are also available from Vascular Technology, Inc., Nashua, N.H. Probes at nominal frequencies of 4 and 8 MHz are recommended for vascular applications. The probe sends ultrasonic waves through the blood vessel and then receives back the reflected waves. Circuitry then generates signals indicative of the speed of the blood. In the case of venous access sites, time-averaging of the signals will likely be necessary because of the pulsing nature of the flow into the patient. When the indicated flow slows significantly or drops off completely, the controller monitoring the Doppler sensor will alert the user or a caregiver by sending a signal indicating the change in flow.

Note that by sensing the actual vein and detecting and measuring blood flow, other conditions can also be discovered. For instance, in placing the needle into the access site, typically an arteriovenous fistula, it is possible to place the needle entirely through the vein, that is, to create an infiltration. With such an infiltration, a significant portion of the blood may not flow through the vein, but will instead enter the body in the area around the vein. If the sensor is placed even a small amount downstream of the access site or fistula, it is possible to detect the difference at least between this flow and previous flows, or between this flow and the flow of blood from the patient. Thus, a flow sensor can be used to detect infiltration.

Figure 8:
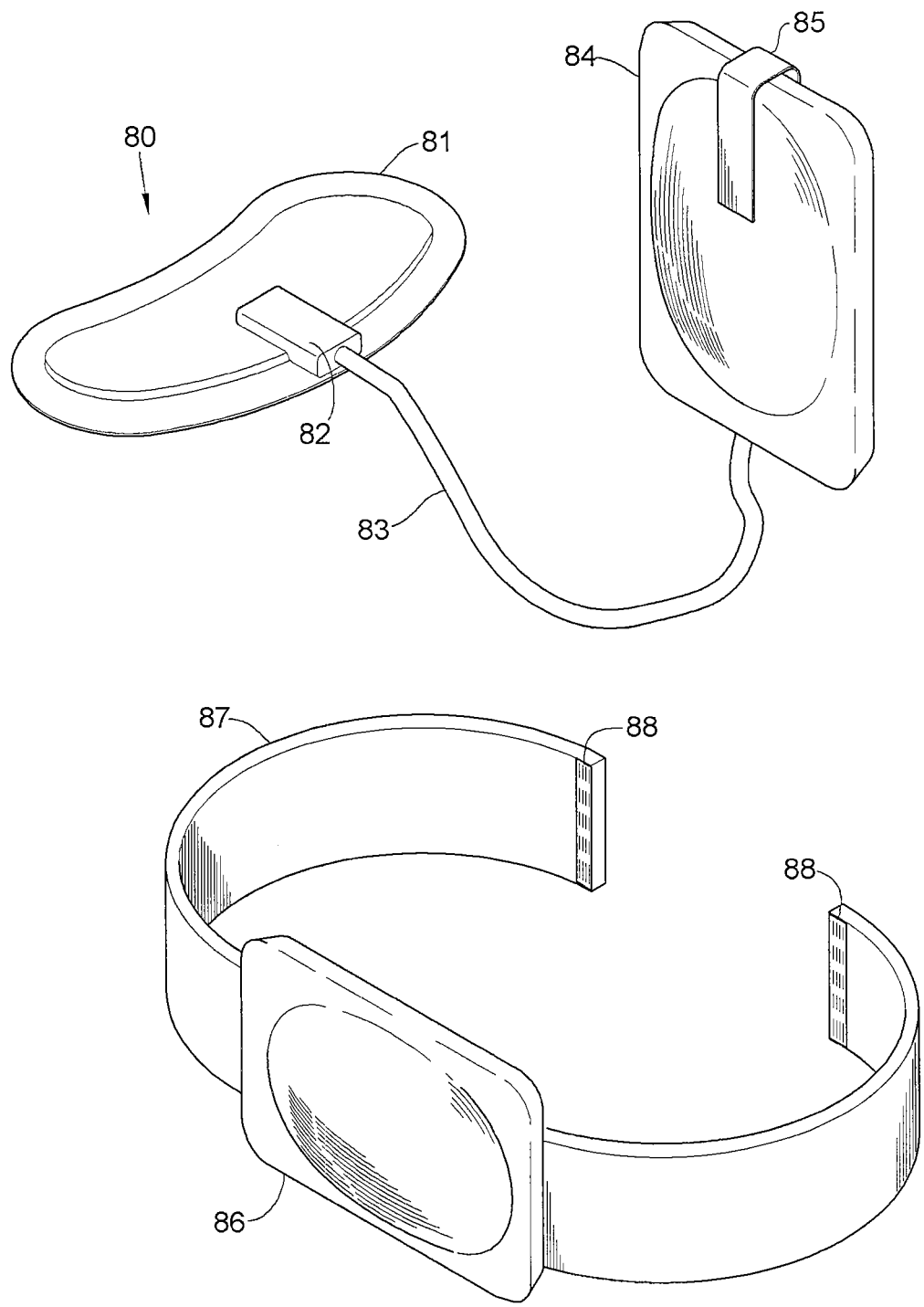
FIG. 8 depicts embodiments with a Doppler flow sensor.

One embodiment of a monitor with a Doppler sensor is depicted in FIG. 8. In this embodiment, a detector 80 includes a butterfly housing 81 with a Doppler sensor 82 is located on the underside of the housing. The housing is intended for mounting near the access site of a patient, and again, the sensor is placed near a periphery of the housing so that it can be placed as close as possible over the return vein or access site of the patient. The sensor is attached via cord 83 to a receiver circuit 84. A clip 85 is furnished to clip the receiver housing to a shirt pocket of the user. In another embodiment, the detector 80 is equipped with a power source and with sufficient signal processing capability that receiver circuit 86 can be mounted wirelessly on the patient's other arm, using a wristband 87 and Velcro® securing strips 88.

Figure 9:
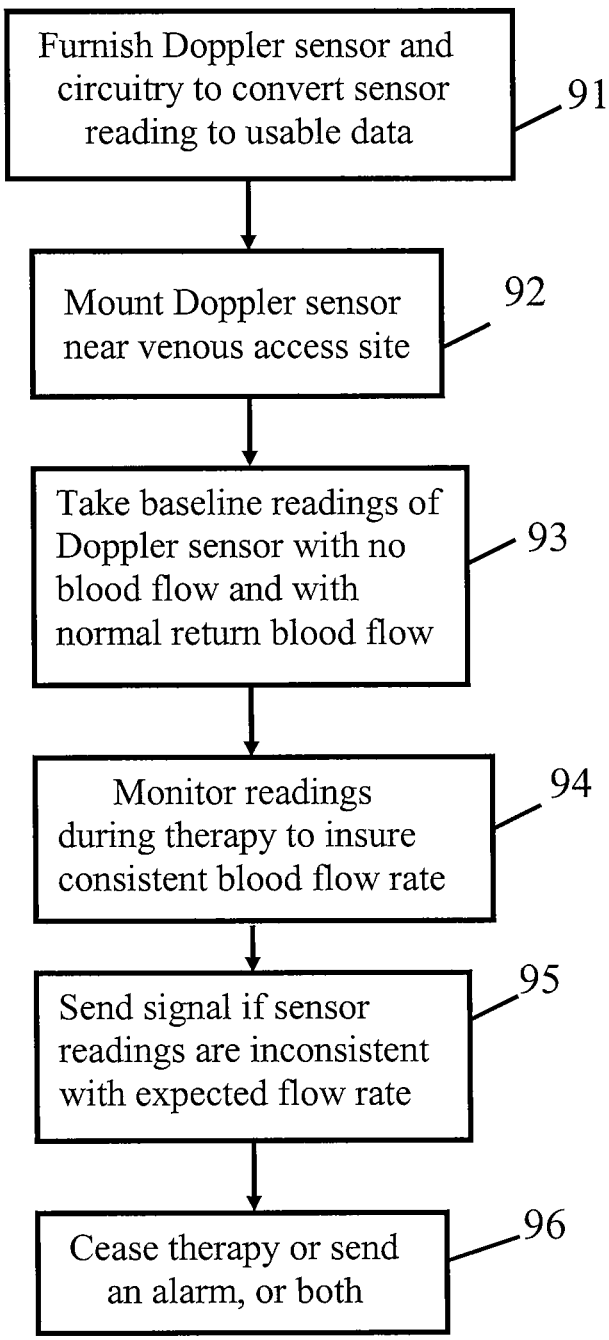
FIG. 9 is a flowchart depicting a method of using a Doppler flow sensor.

The method of using the Doppler sensor is similar to the manner of use of the accelerometer. The method is depicted in the flowchart of FIG. 9. In a first step of the method, a Doppler is furnished 91, along with circuitry to convert the sensor data, typically analog signals, into usable digital data. Other embodiments may simply use analog data, since no conversion to digital is strictly required, although it is customary. The Doppler sensor is mounted 92 near the venous access site, so that the readings of blood movement and flow are clearly discernable. Baseline readings are taken 93, typically with both no flow and with normal return blood flow in order to calibrate the Doppler sensor and to orient the microcontroller or other logic circuit with what are normal and non-normal blood flows.

After therapy has begun, the Doppler sensor is monitored 94 to determine whether the sensor readings are consistent with normal, pulsed blood flow. If the sensor readings are inconsistent with the expected flow, the microcontroller or other logic-device sends 95 a signal. As noted above, the signal may be a signal to cease therapy 96, or may be a signal to raise alert or to send an alarm through a local output device, such as a video screen or a speaker. There are other embodiments using a Doppler sensor to detect blood flow, and this description is not intended to limit the embodiments.

One embodiment includes computer software that controls the therapy machine, such as a hemodialysis machine. The machine may be programmed so that the therapy cannot begin until the accelerometer or Doppler sensor and its expected reading is detected and are within the normal range. That is, the therapy machine or device is interlocked so that the therapy or procedure cannot begin until the required signals from the sensor or sensors are received.

The embodiments described above have been specific in that certain mounts or housings are associated with one sensor or another, such as an accelerometer and flow sensor. It is understood that the sensors may be used with any suitable housing, rather than merely the housing described as particularly suited for a sensor. In addition, most of the sensors have been described as suitable for detecting and measuring venous flow. There is no reason these sensors, and their housings, if any, cannot be used for arterial blood flow. Comparison of arterial blood flow and venous blood flow can lead one to detect infiltration, that is, a puncture of the arteriovenous fistula. There are many other ways to use the sensors and methods described herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An accelerometer-based access disconnect detector, comprising:
    an accelerometer configured for mounting on a patient near an access site, the accelerometer positioned and arranged to measure a pulsatile force of blood returning to the patient;
    signal processing circuitry, the signal processing circuitry operably connected to the accelerometer for receiving indications from the accelerometer indicative of a pulsatile flow rate of blood; and
    a controller configured for receiving readings from the signal processing circuitry and for sending a signal upon a change in the readings, wherein the controller is in communication with or is part of a therapy machine for receiving blood and returning blood to the patient.

2. The access disconnect detector of claim 1, further comprising a communications circuit operably connected to the signal processing circuitry, the communications circuit having a wired or wireless connection to the controller.

3. The access disconnect detector of claim 1, further comprising a flexible pad for mounting at least the accelerometer and the signal processing circuitry on the patient.

4. The access disconnect detector of claim 1, further comprising a memory including at least one look-up table with values for the indications from the accelerometer.

5. The access disconnect detector of claim 1, further comprising an output device operably connected to the controller for alerting the patient or a caregiver.

6. The access disconnect detector of claim 1, wherein the therapy machine is a hemodialysis machine, and further comprising the hemodialysis machine.

7. A method for detecting an access disconnection, the method comprising:
    mounting a sensor on a patient near an access site;
    prior to an extracorporeal therapy, establishing a baseline sensor reading of a blood flow rate of the patient to calibrate the sensor;
    during the extracorporeal therapy, detecting readings indicative of a flow rate of a pulsatile flow of blood through an extracorporeal line with the sensor;
    comparing additional readings during the extracorporeal blood therapy with the readings indicative of the flow rate of the pulsatile flow using a controller; and
    sending a signal via the controller if the additional sensor readings are significantly different from the readings of the flow rate of the pulsatile flow.

8. The method of claim 7, further comprising averaging the additional readings over a period of time before the step of comparing.

9. The method of claim 7, wherein the sensor is a Doppler flow sensor.

10. The method of claim 7, further comprising filtering readings from the sensor of indications of a heart beat of the patient.

11. The method of claim 7, further comprising comparing the additional readings with the baseline reading detected by the sensor.

12. A sensor-based method for detecting blood flow rate, the method comprising:
    mounting a sensor that detects readings indicative of blood flow rate to a patient near an access site;
    detecting no-flow readings using the sensor;
    detecting first readings from the sensor indicative of a flow rate of blood from a pulsing mechanical pump;
    calibrating the sensor using the no-flow and first readings;
    beginning an extracorporeal therapy with the patient;
    detecting additional readings from the sensor during the therapy; and
    providing an alert using an output device if the additional readings are different from the first readings.

13. The method of claim 12, wherein the first readings are baseline readings of blood flow rate of the patient.

14. The method of claim 12, wherein the sensor is an accelerometer or a flow rate sensor.

15. The method of claim 12, further comprising ceasing the extracorporeal therapy if the first readings and the additional readings are different.

* * * * *